United States Patent [19]
Hoult et al.

[11] Patent Number: 5,735,278
[45] Date of Patent: Apr. 7, 1998

[54] SURGICAL PROCEDURE WITH MAGNETIC RESONANCE IMAGING

[75] Inventors: David Hoult; John K. Saunders, both of Winnipeg; Garnette Roy Sutherland, Calgary; Franklin A. Roberts, Winnipeg, all of Canada

[73] Assignee: National Research Council of Canada, Ottawa, Canada

[21] Appl. No.: 616,737

[22] Filed: Mar. 15, 1996

[51] Int. Cl.$^6$ ................................. A61B 5/055
[52] U.S. Cl. ................... 128/653.2; 128/653.5; 324/318; 324/322
[58] Field of Search .................. 128/653.2, 653.5; 324/307, 309, 318, 322

[56] References Cited

U.S. PATENT DOCUMENTS

| | | | |
|---|---|---|---|
| 4,875,485 | 10/1989 | Matsutani | 128/653.5 |
| 4,985,678 | 1/1991 | Gangarosa et al. | |
| 5,008,624 | 4/1991 | Yoshida | |
| 5,477,146 | 12/1995 | Jones | 128/653.5 |
| 5,497,773 | 3/1996 | Kuhara et al. | 128/653.5 |
| 5,577,503 | 11/1996 | Bonutti | 128/653.2 |

FOREIGN PATENT DOCUMENTS 31 40225 A1 of 0000 Germany.

OTHER PUBLICATIONS

MRI Scanner Transport System 8306 Magnetic Resonance Medicine 32(1994) Jul. No. 1 Balmtimore MD US.

*Primary Examiner*—Ruth S. Smith
*Attorney, Agent, or Firm*—Adrian D. Battison; Murray E. Thrift

[57] ABSTRACT

Apparatus is provided for use in surgical procedures comprising an operating table for receiving a patient for surgery and a magnetic resonance imaging system for obtaining images of a part of the patient at a series of times through the surgical procedure for analysis by the surgical team to allow the surgical team to monitor the progress of the surgery. The high field magnet and the operating table are shaped and arranged for positioning of the part of the patient into the magnetic field while the patient remains in place on the table and the magnet is mounted for movement between a first position spaced from the table and the patient thereon to allow the surgical team to carry out the surgical procedure and a second position for applying the magnetic field to the part of the patient. The table remains substantially stationary and only the magnet is moved to a position spaced from an adjacent end of the table to allow the surgical team to move around the adjacent end of table and to each side of the table to access the patient.

20 Claims, 9 Drawing Sheets

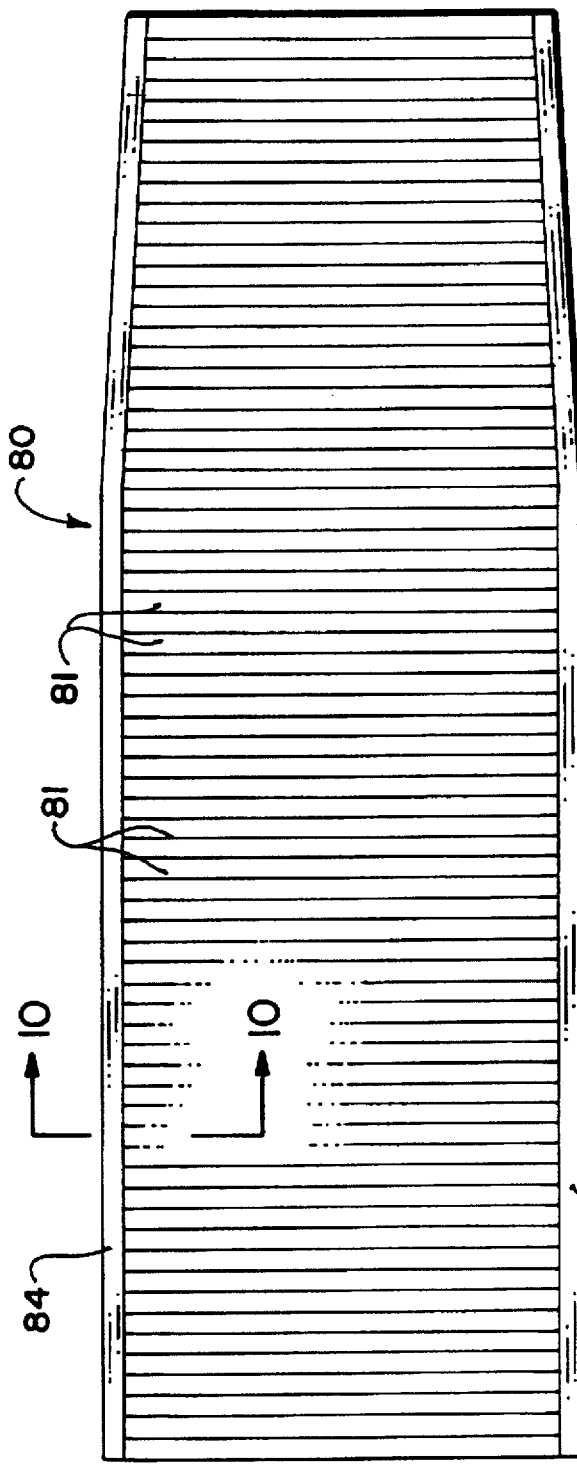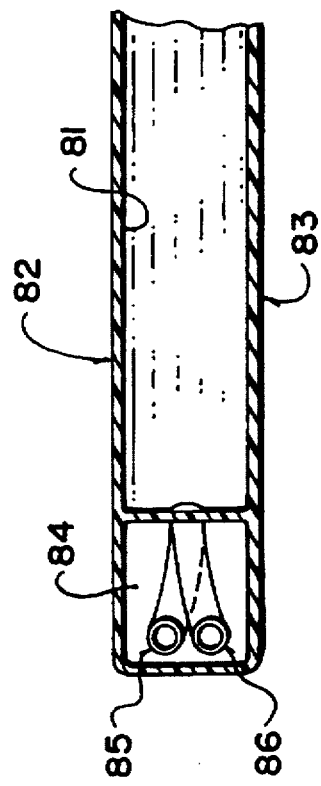
FIG. 9
FIG. 10

SURGICAL PROCEDURE WITH MAGNETIC RESONANCE IMAGING

This invention relates to an apparatus for use in surgical procedures which allows magnetic resonance imaging of the patient periodically during the operation procedure to allow the surgical team to generate repeated images as the operation proceeds.

The apparatus is particularly but not exclusively designed for neurosurgery where the surgical team needs to obtain updated images to determine the progress of the surgery.

BACKGROUND OF THE INVENTION

Modern neurosurgery encompasses the surgical treatment of many complex conditions such as primary intracranial or spinal neoplasms, lesions of the cranium and cranial base, cerebral vascular disorders including arteriovenus malformations, cavernous angiomas and intracranial aneurysms, and inflammatory conditions. Over the past three decades, there have been a number of technological developments that have greatly improved the efficacy and safety of neurosurgery. With improvements in neuroanesthesia, neurosurgeons are now routinely provided with an immobile patient with a needed improvement in hemostasis. The operating microscope, with its improved illumination and magnification, made accessible the undersurface and internal aspects of the brain in such a way that the neurosurgeon is now able to avoid injury to fine vascular or neural structures. Together with the operating microscope, refinements in surgical instrumentation have occurred.

Concurrent with these changes, a remarkable technology explosion took place, fueled in large part by efforts and attitudes within the space exploration industry. Imaging by computerized tomography, magnetic resonance, positron emission tomography, and magnet wave processing provide greatly improved comprehension of brain structure and functional events. The data have provided a more comprehensive understanding for preoperative structural alteration and enhanced safety and precision during operative events. Imaging data have been incorporated into stereotactic space by a number of devices to allow a precise point access and volume comprehension for planning and transcerebral navigation . . . all with striking reduction in operative working corridor size.

An intraoperative magnetic resonance (MR) facility extends these technological developments and would be accompanied by a reduction in operative risk and hence, patient morbidity. Such an improved outcome would ultimately translate into a reduction in the need for hospital resources, including length of stay. Demonstrating such a cost-reducing technological application to neurosurgery is particularly important given the trend towards downsizing medical resources in North America.

A conventional contrast angiogram can be obtained during surgery. However, this necessitates the injection of radioactive contrast reagent into a cerebral artery, with associated risks. Although introduced some 20 years ago, neurosurgeons have been reluctant to adopt this method due to its associated risk and the radiation exposure to both the patient and hospital staff. In addition, the lack of three-dimensional imaging detracts from its utility. Other technologies, such as nuclear medicine computerized tomography also involve either radioactive material or ionizing radiation and therefore place patients, physicians and nurses at risk. Imaging modalities, such as computerized tomography (CT) and intraoperative ultrasound, do not provide adequate information on the cerebal vasculature. Magnetic resonance imaging with a field strength greater than about 0.5 tesla is capable of angiography whereas the above technologies cannot provide this ability.

The General Electric Company (GE) is developing interventional intraoperative MR systems in collaboration with a number of researchers. Siemens has developed what they describe as an interactive MR system. Both these systems are based on an open magnet concept, presenting a number of technical difficulties. The systems are expensive, and attempt to provide an MR unit which can function during several types of different operations.

The present GE system in the field, is based on a magnet which is a double doughnut shape with the patient being perpendicular to the plane of the two doughnuts. This system permits only two medical staff to be in close attendance standing in between the two doughnuts. The field strength is 0.5 tesla, and the patient and the operating staff are always in the magnetic field. It is doubtful that the double doughnut magnet can be made to operate at fields higher than 0.5 tesla, which means MR angiography is essentially eliminated as a viable examination by such a system thus significantly decreasing its utility during neurosurgery. Furthermore, all implements used in the surgery, for example the microscope and scalpels are in the magnetic field and thus must be specially designed to be compatible with this environment. Yet further, neurosurgery generally requires a large team of staff most of whom need access to the patient and hence the limited access provided by the magnet shape is a severe limitation which will likely reduce the acceptability of the device.

The Siemens open magnet concept was designed for performing surgery while the person is in the magnet. This arrangement therefore has the same disadvantages as the GE device.

Proposals are presently being made for an arrangement in which the magnet is conventional and therefore maintained stationary. However this requires that the patient be moved into the magnet. This movement is problematic since the patient is in most cases fitted with monitors and intubated so that any movement may place the patient at unnecessary risk.

SUMMARY OF THE INVENTION

It is one object of the present invention, therefore, to provide an improved apparatus for use in surgical procedures which allow repeated magnetic resonance imaging with derivatives such as angiography and spectroscopy of the patient as desired at various stages through the operation without hindrance to or restriction of the medical staff and with all the benefits that pertain to the use of a high field magnetic resonance imaging system.

According to one aspect of the invention there is provided an apparatus for use in surgical procedures comprising: an operating table for receiving a patient for surgery; and a magnetic resonance imaging system for obtaining images of a part of the patient at a series of times through the surgical procedure for analysis by the surgical team to allow the surgical team to monitor the progress of the surgery, the system comprising: a magnet for generating high magnetic fields and its gradients a control system for controlling and varying the magnetic fields; and a radio frequency (RF) transmission and detection system for eliciting and detecting nuclear magnetic resonance signals from the part of the patient, in response to the magnetic fields the system including an RF probe for locating adjacent to the part of the patient; and a computer and display monitor apparatus for decoding and displaying the detected signals; the magnet and table being shaped and arranged for positioning of the part of the patient into the magnetic field while the patient remains in place on the table; and means mounting the magnet for movement between a first position spaced from the table and the patient thereon to allow the surgical team to carry out the surgical procedure and a second position for applying the magnetic field to the part of the patient.

Preferably the table and mounting means are arranged such that the table and the patient remain substantially stationary and only the magnet is moved.

Preferably the table and mounting means are arranged such that the magnet is moved to a position spaced from an adjacent end of the table to allow the operating team to move around the adjacent end of table and to each side of the table to access the patient.

Preferably the magnet is shaped to define an inner substantially cylindrical bore into the center of which the part of the patient is inserted and wherein the table includes an upstanding mounting base and a table top mounted thereon, the table top having a cantilever portion extending from the base into the cylindrical bore.

There exists the danger that the acceleration and deceleration of a superconducting magnetic resonance imaging magnet, necessary for rapid movement to facilitate a minimal imaging time period, could cause damage to the magnet or could even result in the energy contained in the magnet being explosively released. Further, movement of the magnet causes changes in its field. Such changes may continue for seconds or even minutes after movement ceases, thereby substantially degrading images obtained and rendering them worthless. Thus the magnet must be capable of withstanding the desired acceleration and deceleration, and preferably, the magnet is equipped with means for stabilisation of its field that operates satisfactorily in the presence of those field changes required for the imaging procedure.

In order to achieve the movement of the magnet over the patient and the table, the design of the table is important. Thus the table preferably includes means for tilting the table top about an axis transverse to the table top so as to tilt the patient to an angle sufficient to raise the head of the patient to allow neurosurgery, the table top and the cylindrical bore being arranged such that the head of the patient can be located centrally in the bore while the tilted table top projects into one end of the bore. Also the table top preferably includes a hinged portion at the end thereof for supporting the head of the patient, the hinged portion being pivotal about an axis transverse to the table top and spaced outwardly from the base so as to raise only the head and shoulders of the patient to a height sufficient to allow neurosurgery. Also the cantilever portion preferably includes a flat plate for receiving the patient and a channel attached to an underside of the plate and narrower than the plate to support the plate while minimizing the dimensions of the table top to fit in the circular cross-section of the bore.

Yet further, the table preferably includes a mattress thereon comprising a plurality of parallel inflatable tubes transverse to the table and means for inflating and deflating alternate ones of the tubes so as to vary the pressure points on the patient from the mattress.

Yet further, the table preferably includes parts thereof manufactured from a highly electrically resistive and non-ferromagnetic material, such as titanium, which is preferably coated with a layer of low electrically resistive material, such as copper.

In order to achieve an effective system, that parts of the RF transmission and detection system including the RF probe, that is placed about the patient should be arranged so that they do not interfere with the operation or require any movement of the patient. For this reason the RF probe is shaped and arranged such that it can be actuated in the magnet and such that it can allow access to the part of the patient for the surgical procedure outside the magnet without the necessity for moving the part of the patient.

The RF probe preferably comprises a first probe element for positioning on one side of the part and a second probe element for positioning on an opposed side of the part, the first element being removable to allow access to the patient for the surgical procedure. Preferably the elements are free from wired electrical interconnection so that the first element can be removed without disconnecting any wire interconnection. Preferably the first and second elements each comprise a plurality of parallel planar coils and there is provided means for moving at least one of the coils for tuning and matching the probe.

For simplicity of installation an RF shielding layer to shield the RF probe from surrounding variations preferably comprises an electrically conductive flexible fabric layer wrapped around those parts of the patient and table which are outside the magnet.

As the magnet is moved in this procedure there is preferably provided means for stabilizing the field of the magnet after movement of the magnet and prior to imaging, the stabilizing means comprising means for detecting changes in the field and means for controlling the field of the magnet.

Preferably the detecting means comprises a coil mounted inside the inner bore of the magnet and coaxial therewith and a conductive layer coaxial with the bore and extending along the bore to a distance greater than the coil, the conductive layer being in capacitive electrical connection with the coils and being formed of a material which is non-ferromagnetic, and has an electrical resistance and thickness selected so as to allow currents in the coils which have sufficient bandwidth to detect changes in the field and so as to not interfere with the variation in the field necessary for the imaging techniques.

Preferably the RF shielding layer to shield the RF probe from surrounding variations includes the conducting layer.

BRIEF DESCRIPTION OF THE DRAWINGS

One embodiment of the invention will now be described in conjunction with the accompanying drawings in which:

FIG. 9 is a top plan view of a mattress for laying on the operating table of FIG. 1.

FIG. 10 is a cross sectional view along the lines 10—10 of FIG. 9.

In the drawings like characters of reference indicate corresponding parts in the different figures.

DETAILED DESCRIPTION

Figure 1:
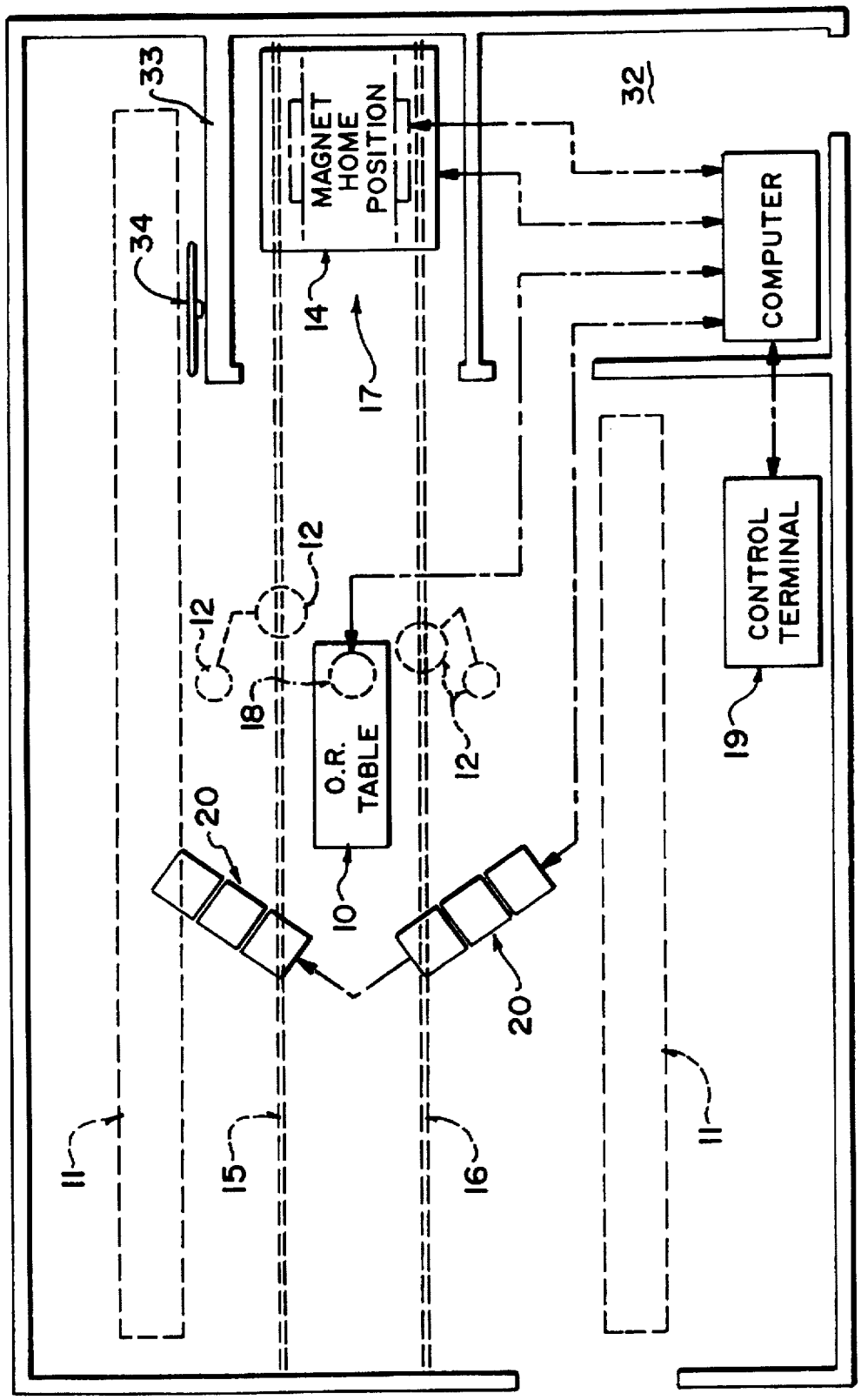
FIG. 1 is a top plan view of an operating room including the apparatus according to the present invention.
Figure 2:
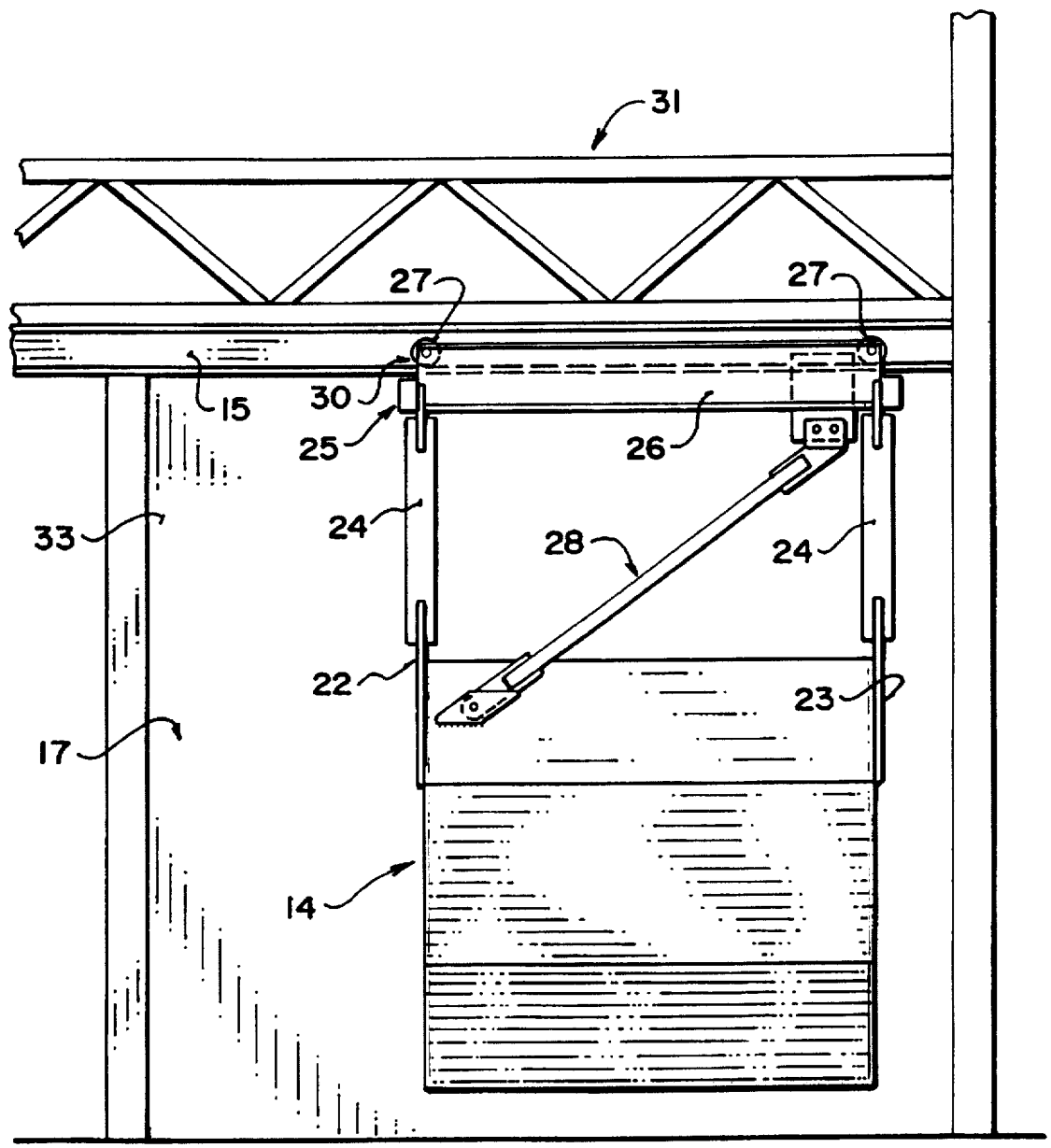
FIG. 2 is a side elevation view of the magnet and support system therefor of FIG. 1 in the home position.
Figure 3:
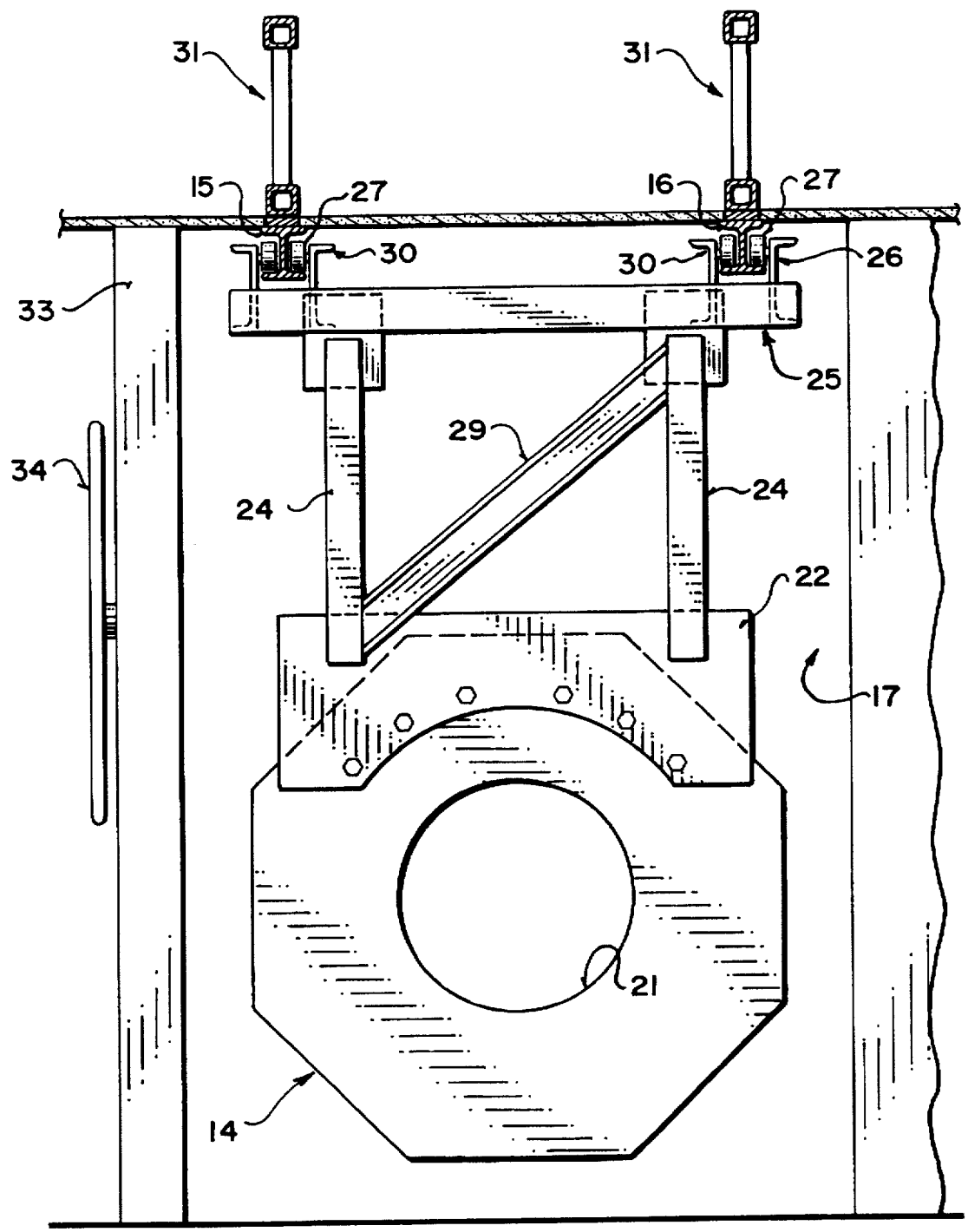
FIG. 3 is a rear elevational view of the magnet and support system therefor of FIG. 1.

The operating room (OR) shown in FIG. 1 comprises an operating table 10 on which the operation is carried out located generally in the center of an operating room with suitable lighting provided by fluorescent lights 11 and ceiling mounted lighting 12. A magnetic resonance imaging magnet 14 is mounted in the room for movement longitudinally in the room on ceiling support tracks 15 and 16 thus providing a home position 17 for the magnet and allowing the magnet to move to an operational position cooperating with the table 10.

The imaging system further includes an RF detection probe assembly 18 which is located at the patient on the table 10 together with a control system which is mounted in a separate computer room 32 to maintain sterile conditions in the OR. The control system effects control of the magnet 14 and control of the signals applied to the RF probe together with analysis of the signals detected by the RF detector 18 to provide control of the imaging system and to provide output of an image on one or more of a series of monitors located above the table 10 for viewing by the surgical team. An input terminal 19 is located in the OR for access by the surgical team. The control system also provides control for angiography or spectroscopy in conventional manner.

The monitors 20 are of a type using an LCD display system so as to be resistant to magnetic fields generated by the magnet. The displays can include a display of the latest image from the MRI system, a display from the conventional surgical microscope together with further displays suitable to the surgical team.

The computer room is preferably shielded from the OR to reduce electromagnetic interference with the probe.

The magnet 14 is a commercially available, shielded MRI magnet of a type which is arranged to accept the stresses of the acceleration and deceleration involved in moving the magnet. The magnet defines an inner cylindrical bore 21 of a diameter of the order of 80 cms which provides a usable space within the magnet which is cylindrical and has a diameter of the order of 65 cms. The magnet can provide a field strength of 1.5 tesla at the center of the bore. The magnet has a length of the order of 1.5 meters, short enough to allow the magnet to be moved so that the part of the patient to be imaged is in a position at or substantially at the center of the bore both longitudinally and transversely. The magnet thus fully surrounds the patient on the operating table and the patient can enter into the bore only from the ends so that the amount of space for movement within the bore is very limited. In order to provide the necessary field strength for effective imaging and angiography or spectroscopy, which field strength is normally of the order of 1.5 tesla, the magnet must necessarily fully surround the part of the patient to be imaged and define the full cylinder surrounding that part and extending to both sides of the part.

The details of such magnets are well known to one skilled in the art and therefore will not be included herein.

The magnet 14 is carried on a pair of end plates 22 and 23 bolted to the end face of the magnet in a manner which allows the magnet to be suspended from the end plates. The end plates are welded to vertical support posts 24 with two such posts for each plate spaced toward each end of each plate and extending upwardly from the plate to a rectangular frame structure 25 defined by horizontal and longitudinal beams 26.

The frame 25 is supported on the rails 15 and 16 by rollers 27. Thus each rail is engaged by two pairs of rollers spaced along the length of the frame. Each rail comprises an I beam with the rollers running on top of the bottom flange of the I beam so as to control the movement of the magnet in an accurate longitudinal movement with very restricted side to side movement. The structure includes stiffening braces 28 and 29 which retain the frame structure supposing the end plates 22 and 23 rigid and rectangular so as to prevent any swaying or twisting of the magnet as it moves along the rails. The rollers 27 are carried in suitable brackets 30 mounted on the top of the frame 25. Each of the I beams 15, 16 is welded to a respective truss 31 attached to the top flange of the I beam and arranged to bridge from suitable supporting structure in the walls at the ends of the operating room. Thus the room is free from vertical supporting posts for the rails 15 and 16 allowing the magnet to move in effect along the full length of the room and certainly from the home position adjacent to one end wall of the room to the center of the room for cooperation with the operating table. The magnet can also be moved vertically by adjustment of the brackets 30 to accommodate different heights of the table.

As shown the home position is located between a computer room 32 and a vertical wall 33 so that the magnet is parked in an area separated away from the remainder of the room. A hand wheel 34 is provided on the wall 33 and cooperates with a chain drive system for moving the magnet from the home position to the imaging position and back to the home position. The hand wheel can be replaced by a suitable drive motor if required.

Figure 4:
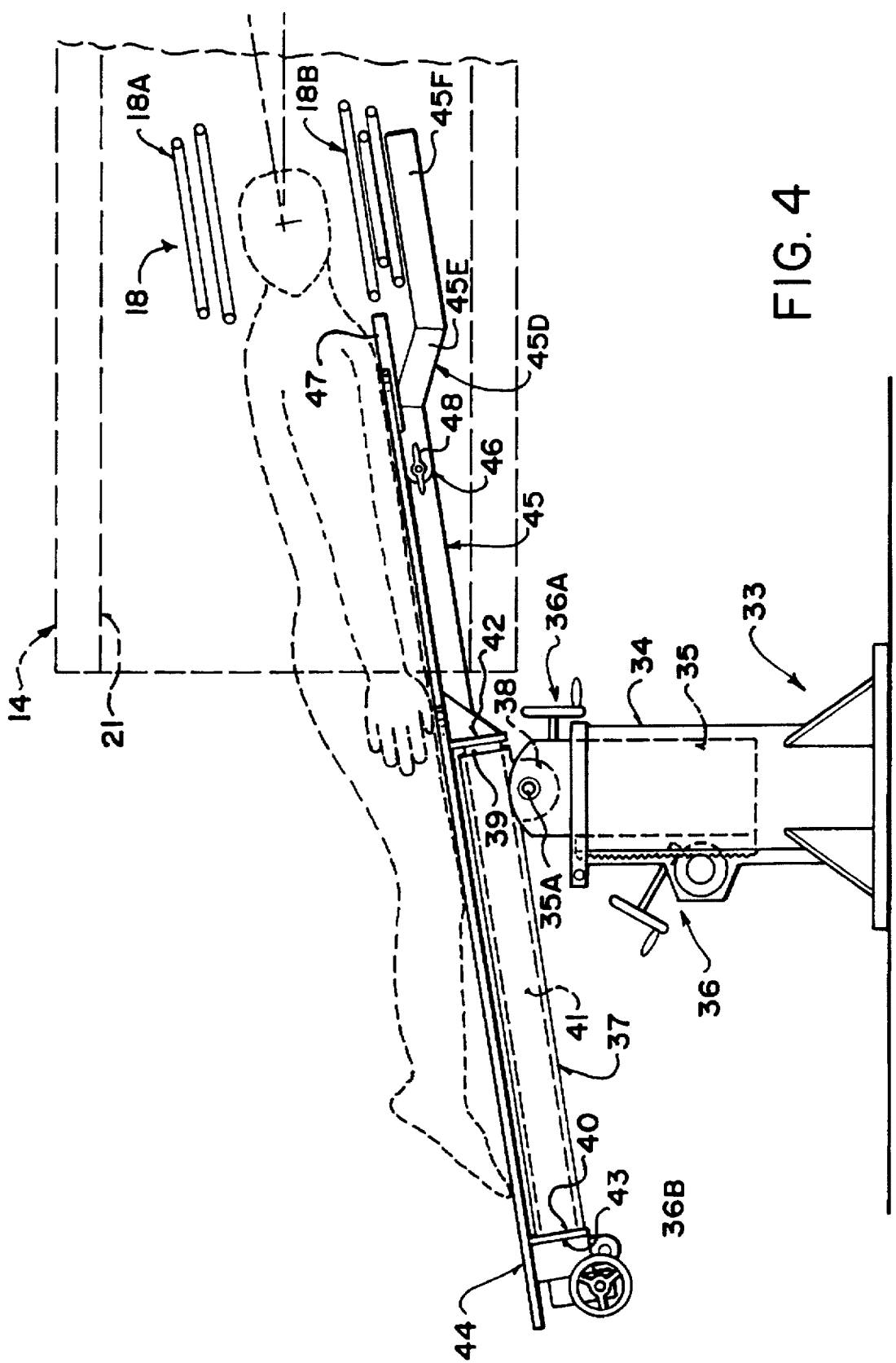
FIG. 4 is a side elevational view of the operating table of FIG. 1 showing the magnet in position for imaging.
Figure 5:
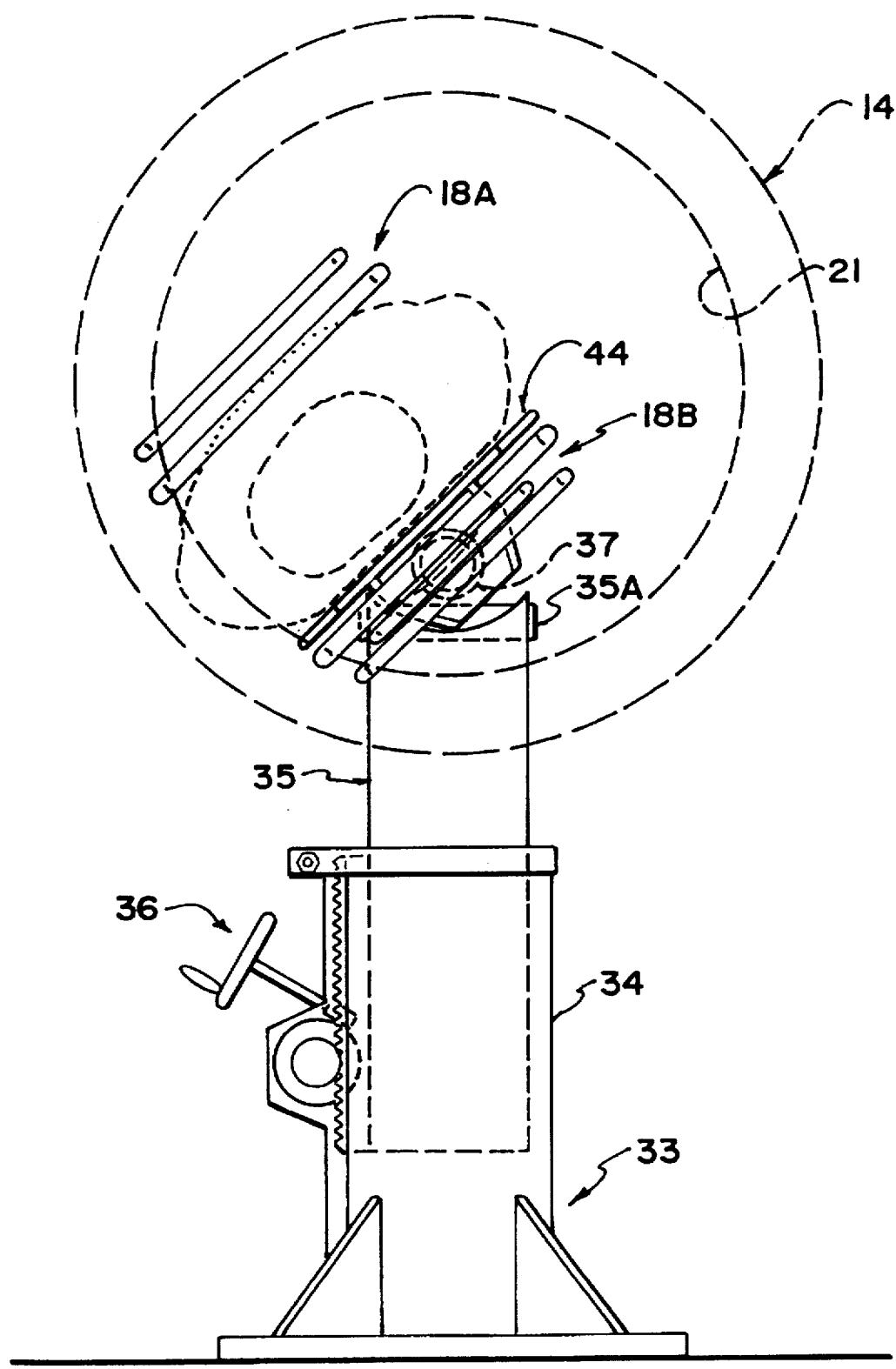
FIG. 5 is an end elevational view of the operating table and magnet of FIG. 4 showing the operating table in a position tilted about a longitudinal axis.
Figure 6:
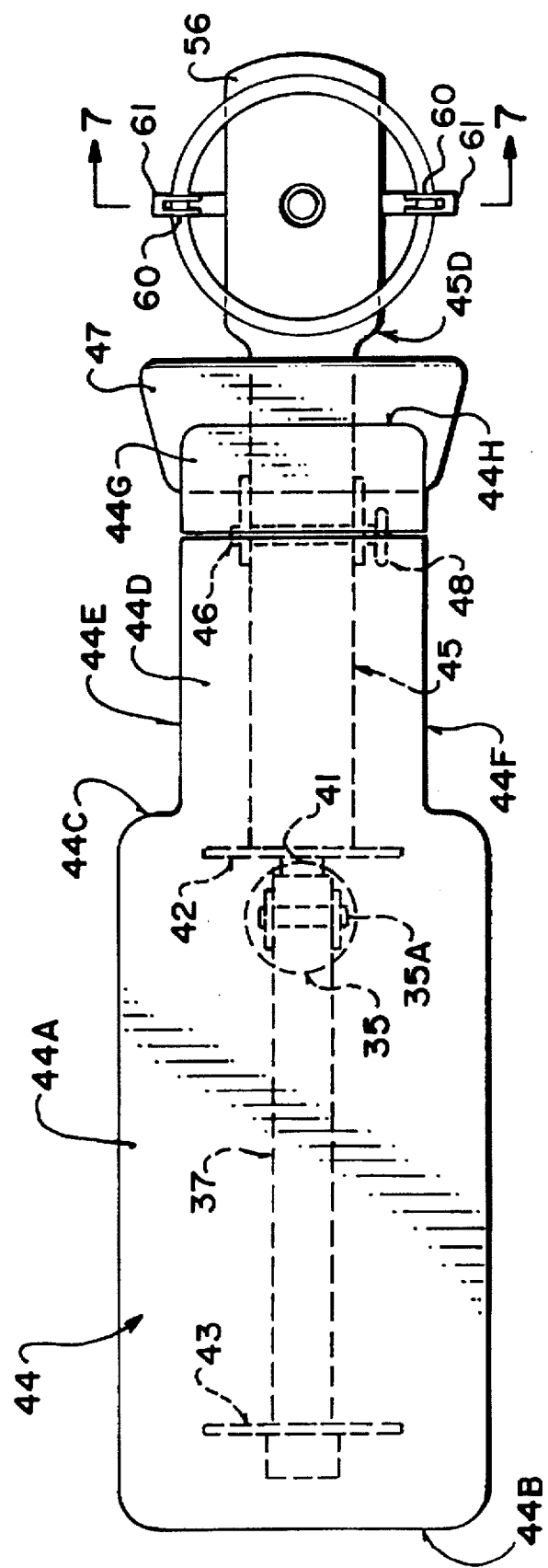
FIG. 6 is a top plan view of the operating table of FIGS. 4 and 5.

The operating table is shown in FIGS. 4, 5 and 6 and comprises a pedestal base 33 mounted on the floor and upstanding therefrom. The pedestal base provides a sleeve portion 34 at the upper end receiving a vertically adjustable post 35 which can be raised and lowered by an adjustment system 36 in the form of a worm and wheel with the worm driven by a hand crank. At the top of the post 35 is provided a transverse support pin 36 carrying a cylindrical sleeve 37 on a lug 38. The sleeve 37 is extended at right angles to the pin 36 and extends from a forward end 39 of the sleeve to a rearward end 40 of the sleeve. The lug allows the sleeve to pivot about the pin 36 and thus about the axis of the pin which is transverse to the length of the table and horizontal with the adjustment of the angle of the sleeve be effected by adjustment mechanism 36A similar to the mechanism 36.

Figure 7:
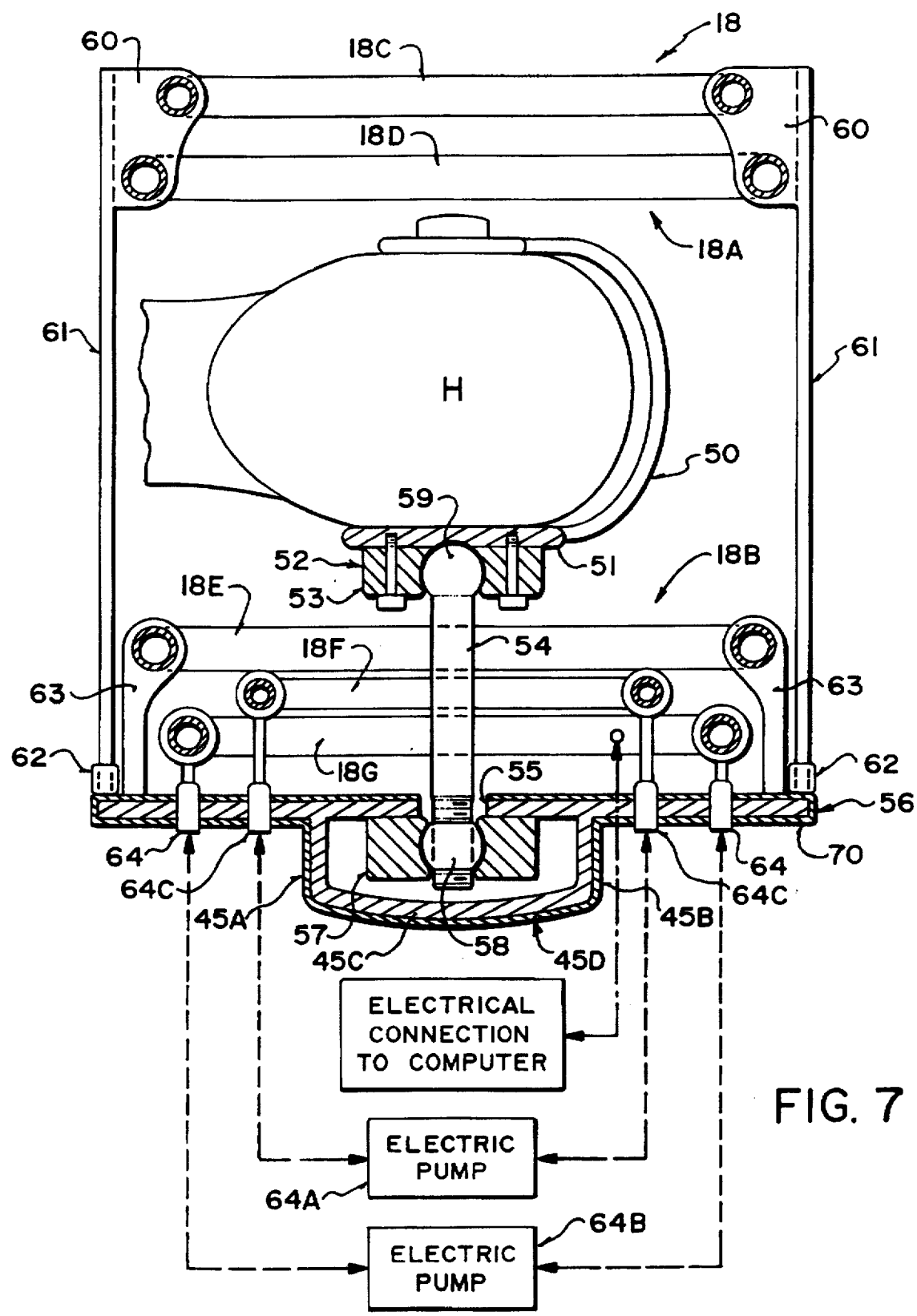
FIG. 7 is a cross sectional view on an enlarged scale taken along the lines 7—7 in FIG. 6.

Inside the sleeve 37 is provided a beam 41 which can rotate about the longitudinal axis of the sleeve 37 with the beam projecting out beyond each end 39, 40 of the sleeve 37. The angle of the beam within the sleeve is adjusted by a hand wheel adjustment system 36B similar to the adjustment 36. The beam 41 is attached at its forward end to a plate 42 and its rearward end to a plate 43 with the plates 42 and 43 being parallel and transverse to the length of the table. On top of the plates 42 and 43 is mounted a longitudinally extending flat metal table top 44. As shown in FIG. 6, the plate forming the table top includes a first generally rectangular section 44A with ends 44B and 44C together with a further narrower section 44D which projects outwardly from the end 44C. The main rectangular portion and the narrow portion are formed of one plate so as to remain flat and rigid. The main plate is supported in the flat condition by the transverse support plates 42 and 43 and by a beam 45 which is welded at its rear end to the plate 42 and projects along the narrow portion 44D spaced inwardly from side edges 44E and 44F thereof. The beam 45 as shown in cross section in FIG. 7 is defined by a channel with vertical sides 45A and 45B and a convexly curved base 45C. The top edge of the sides 45A and 45B are welded to the plate such that the channel and the plate together define a structural beam providing sufficient strength so that the portion of the table projecting forwardly from the post 35 and the pin 36 is cantilevered. The shape of the beam with the channel being narrower than the plate allows the structure to fit in the core of the magnet most efficiently since an arc of diameter of the inner bore 21 just passes through the edges of the plate and the lowermost point of the channel at the middle of the channel.

The beam 45 is divided into a first portion rigidly connected to the plate 42 and a second hinged portion 45D which is pivotally connected to the first portion at a pivot pin 46. The plate 44 is similarly flat and rigid up to the pin 46 and at the pin is divided into a second hinged portion 44G which lies on top of the hinged beam portion 45D. At a forward edge 44H of the portion 44G is attached an additional plate 47 for supporting the shoulders of the patient and formed from a sheet of Teflon or similar material to reduce the amount of metal adjacent the probe. Underneath the plate 47 the beam 45D includes a canted portion 45E extending downwardly which connects to a further portion 45F which is parallel to the main portion of the beam but spaced downwardly therefrom.

Figure 8:
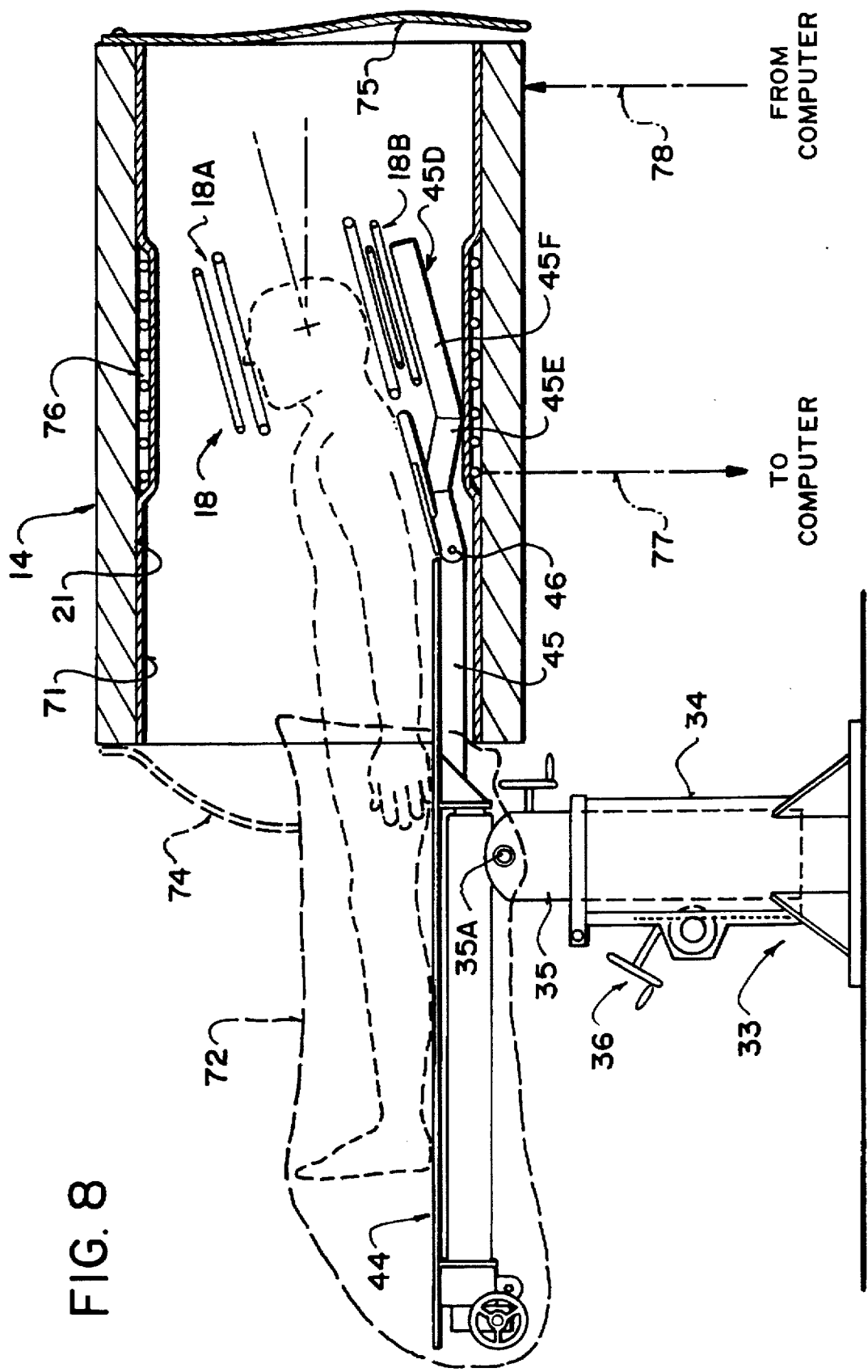
FIG. 8 is a view similar to that of FIG. 4 showing the operating table in an adjusted position and showing further details of the magnet shielding.

The angle of the portion 45F of the beam relative to the main portion of the beam can be adjusted by actuating a manual clamp system indicated at 48 which allows the portion 45F to be adjusted and then clamped in position as it will be appreciated by a comparison of FIGS. 4 and 8.

As shown in FIG. 5, the post 35 can be raised to an increased height to accommodate the position of the magnet or to accommodate the requirements of the surgical team. This adjustment is effected by the crank system 36. In addition the angle of the plate 44 about the longitudinal axis of the table can be adjusted by actuating the crank 36B so as to tilt the table top to one side as shown or to the opposed side as required in order to tilt the angle of the patient to accommodate the requirements of the surgical team during surgery. When tilted, the patient will be strapped in place on the table top or plate 44.

The present system is particularly but not exclusively designed for use in neurosurgery and it is well known that in neurosurgery the head of the patient must be raised above the heart of the patient by a predetermined vertical distance so as to maintain the hydrostatic pressure at the operation site in the head within predetermined required limits dictated by the patient's heart.

As shown in FIG. 4, with the patient body lying prone on the table, this height requirement of the head is obtained by tilting the table about the pin 36 by an angle of the order of 10°. In this position, the beam portion 45F is maintained parallel to the main portion of the beam. The outline of the magnet is shown in dotted line in FIG. 4 and it will be appreciated therefore that the angle of the table lifts the portion 45F of the beam slightly upwardly and thus allows it to just penetrate within the bore of the magnet. In this position and at the required height of the post 35, the bottom of the beam just clears the edge of the bore at the mouth of the magnet when the magnet reaches substantially to the post 35. This allows the patient to penetrate to a position centrally of the magnet while the patient remains unmoved and the table remains in fixed position set before the magnet is moved into place.

In FIG. 8, the patient is shown lying supine. In order to achieve the required height of the head of the patient above the heart of the patient, the table top is adjusted relative to the pin 36 so that the main portion of the table top is horizontal. In this position however the beam portion 45F is adjusted about the pin 46 so that it is cranked upwardly by an angle of the order of 10° thus lifting the head of the patient supported on the beam, as described hereinafter, relative to the thorax of the patient which remains lying on the horizontal table top. For this purpose the pin 46 is located approximately midway along the length of the beam so that it is positioned just forwardly of or underneath the part of the thorax where the heart is located. The adjustment of the angle of the portion 45F lifts the junction between the beam portions 45E and 45F upwardly to a height approximately equal to the main portion of the beam so that the beam can just be inserted into the magnet while just clearing the lowermost surface of the magnet, again reaching the head of the patient to a position centrally of the magnet.

Turning now to FIGS. 6 and 7 there is shown the arrangement for supporting the head H of the patient on the beam portion 45D and also the construction of the RF probe 18 which surrounds the head H.

The mounting of the head includes a conventional head clamp 50 which is well known and commercially available and therefore is shown only schematically. The clamp 50 includes a bottom side plate 51 which is bolted to a clamp mount 52 attached to the beam portion 45D. The clamp mount comprises an upper mounting plate 53 carried on a post 54 which projects through a hole 55 in the top plate 56 of the beam portion 45D. The lower end of the post 54 is mounted in a support member 57 attached to the underside of the plate 56 and the support member 57 allows vertical sliding movement of the post 54 and also two degrees of swiveling movement about a spherical bearing 58 within the support member 57. The post 54 can thus move vertically and can also tilt side to side and front to back as required to locate the side plate 51 of the clamp 50 in the required orientation to hold the head of the patient at the orientation determined by the surgical team. The plate 53 of the clamp support also includes a spherical bearing 59 which allows tilting of the plate 53 and therefore the head clamp. The head of the patient is thus supported above the beam portion 45D but is spaced therefrom by the length of the post 54.

For convenience of illustration the details of the mounting arrangement for the head and the support for the RF probe are omitted in FIGS. 4, 5, and 8.

In order to allow access by the surgical team to the head during the operating procedure, the RF probe is divided into two parts including an upper section 18A and a lower section 18B.

The upper section 18A comprises two parallel, circular tuned coils 18C and 18D which are located above the head when required for imaging. The lower part 18B includes three coils 18E, 18F and 18G. The coils are of differing diameters as shown. Thus the coils 18D and 18E are approximately of the same diameter and the coils 18C and 18G are approximately of the same diameter and smaller than the coils 18D and 18E. The coil 18F is smaller than both of the coils 18E and 18G and is located between those coils.

The coils 18C and 18D of the upper part 18A are mounted rigidly on brackets 60 which engage the coils at spaced positions around the diameter of the coils and holds those coils in fixed relation relative to one another. The number of brackets can of course be varied but as shown there are two such brackets arranged at 180° spacing. In practice three such brackets are likely to be used for maximum stability.

Each of the brackets includes a connection leg 61 which extends downwardly from the respective bracket and engages into a quick release fastening mechanism 62 carried on the plate 56. Thus the upper detection member 18A can be readily engaged into place by engaging the legs on the base plate and can be readily removed simply by lifting the upper coils and the legs vertically upwardly and lifted over the patient to be removed for storage when not required.

Very quickly, therefore, the upper coils can be placed in the required position for the necessary detection process when the patient is to be located in the magnet and very quickly the upper coils can be removed from the patient when the imaging process is complete and the surgical team is to return to the operation.

The coils 18E are mounted on brackets 63 which hold those coils in fixed position with the brackets being directly attached to the base plate 56. The lower detection portion thus remains in place during the operation and does not interfere with the surgeon's access to the operation site. It can however be detached if necessary.

The coil 18G is mounted on hydraulic lifting devices 64 which can move the coil vertically to effect tuning of the RF probe. The coil 18F is mounted likewise on hydraulic lifting devices 64C to effect matching of the RF probe. The hydraulic actuators 64 and 64C are formed of a plastics material and each comprises a cylinder attached to the base plate and a piston with piston rod attached to the coil by suitable attachment collar. The supply of a suitable fluid to the cylinders therefore actuates vertical movement or twisting movement of the coils 18G and 18F both upwardly and downwardly under the control of a pumps 64A and 64B. The pumps are controlled by the computer 19 with additional electronic circuitry (not shown) so as to provide immediate and automatic tuning of the RF detection system.

The only electrical connection to the coils is a connection which extends to the coil 18F and from that coil to the receiving portion of the RF detection system and thence to the computer for detecting the output of the detection system. There is no electrical connection between the coils in the sense that there is no wired connection but there is of course an induction effect which allows the RF probe to operate.

Further details of this RF detection system are disclosed in a paper co-authored by one of the inventors, published in 1990 in the Learned Journal "Magnetic Resonance in Medicine" and entitled "A High Sensitivity, High B1, Homogeneity Probe for Quantitation of Metabolites".

As shown and described herein, one set of coils is mounted below the head and one above the head. However it will be appreciated that different arrangements can be used in a probe which splits into two parts to allow the part to be removed readily for access during surgery. For example the coils may be mounted vertically, each on a respective side of the head.

In order that the operating table is suitable for penetration by the very high magnetic field of the magnet when the latter approaches, it is necessary that the table be manufactured of materials which are consistent with this requirement. Thus the table must be non-ferromagnetic. Yet further the table must have a high electrical resistance. Finally the table must have sufficient structural stability and strength to accommodate the forces involved. The material particularly selected for these requirements is Titanium. The high electrical resistance is necessary is in order to prevent the generation of high currents in the table as the magnet approaches. Such currents in turn can generate large forces which can cause potentially dangerous movement of the table.

However the titanium with its high electrical resistivity is inconsistent with efficient operation of the RF probe. In order to overcome this inconsistency, the titanium forming the structural element of the base plate 56 and the portion of the beam 45D adjacent the base plate is covered with a layer 70 of copper which has a thickness of less than 10 µm. This copper layer is insufficient to allow high currents to form as the magnet approaches yet is sufficiently thick (greater than five times the RF skin depth) to avoid deterioration of the efficiency of signal detection by the probe.

Turning now to FIG. 8, RF shielding for the magnet is of a type which is localized to the area of the magnet rather than the technique which is conventionally used which is to provide a copper lining to the room in which the magnet is located. In this arrangement, the shielding comprises three elements. The first element comprises a layer 71 of suitable thickness and resistivity applied on the inside of the bore 21 of the magnet 14. The conducting layer 71 is thus cylindrical and covers the whole of the inside surface of the bore. This is protected by a plastic covering layer (not shown). The second element of the shielding comprises an electrically conductive fabric bag 72 which wraps around the lower part of the patient. The bag includes an open mouth 73 of the bag which is open to allow the bag to be wrapped around the patient and over the lower part of the table. The bag is thus basically closed apart from the mouth 73. However a slit in the area of the post 35 is provided to allow the bag to be wrapped around the post and closed by suitable closures. Electrically conductive fabric of this type is currently commercially available and suitable such fabric has an electrical surface resistance of the order of 1 ohm per square.

The bag remains in place on the patient during the operation procedure and includes a series of electrical connecting straps 74 which extend from the bag and connect to a suitable frame element on the magnet 14 at spaced positions around the bag. The straps are thus connected when the magnet is brought into place and are disconnected when the magnet is to be removed so that the magnet can be moved away and the bag left in place on the patient.

The third element of the shielding comprises a curtain 75 of the electrically conducting fabric which is suspended over the open mouth of the magnet at the end opposite to the patient. In this way the bag, the foil layer and the curtain provide localized shielding to prevent stray signals from interfering with the detection by the RF detection system 18.

As the magnet is moved from its home base to the operating table for the imaging process, the magnet will move past areas of different ferromagnetic content which will effect the magnetic field within the magnet for sometime afterwards. Acceleration and deceleration may also effect the field. As is well known, in the conventional MRI process, the magnetic field is varied in a very precise manner, and any extraneous variations which are not controlled will seriously affect the ability of the system to generate accurate images. It is important therefore that the magnetic field be stabilized to the desired value quickly before the desired variations are applied, and that it remain stabilized to that value following the desired variations.

It is further important that the stabilization occur within a short period of time since there is a very limited period during which the imaging can take place. In the operating procedure, the surgical team takes periodic breaks of the order of 10 to 15 minutes in time and it is essential that the imaging be completed including all the steps of moving the magnet and applying the imaging elements, within this period of time so as not in any way to interfere with the surgeon's normal procedures.

It is important therefore that the stabilization of the magnet occur within the first few seconds in order that the imaging can then proceed in conventional manner with the magnet properly stabilized.

For this purpose, electrical coils 76 are provided within the bore 21 for detecting the magnetic field and particularly any variations therein. These coils detect the rate of change of the magnetic field with the necessity that the output from the coils be integrated in order to obtain data relating to the changes in the magnetic field. The output from the coils is thus communicated to the computer along a line 77 for these calculations to occur, or integrated in an analogue manner familiar to those skilled in the art. The field of the magnet is controlled by a supply of current to the magnet elements which may include a field-shift coil, along a line 78 from the computer. The details of the control are well known to one skilled in the art and accordingly will not be described herein.

In order to enhance the bandwidth of detection by the coils 76, the conducting layer 71 capacitively couples to the coils to produce a transmission line, and is electrically connected to the coil ends with conducting characteristic resistances so as to provide the necessary conditions for the coils to respond rapidly to the changes in the magnetic field by the production of representative voltages between the coil's ends. However the conducting layer, which may be for example foil, cannot interfere with the necessary variations in the magnetic field which are essential for the imaging process to occur. Nor can it interfere with the homogeneity of the magnetic field. For the latter purpose the layer must be non-ferromagnetic.

Furthermore, the thickness and resistivity must be selected in accordance with the following formula in order to obtain the necessary characteristics set forth above. It may be shown that if $\tau$ is the time constant of changes in the magnetic field associated with the imaging process, a is the radius upon which the foil is placed, $\rho$ is the foil's resistivity and $t$ is its thickness, then:

$$\rho/t >> 4 \times 10^{-7} a/\tau$$

Thus if a=0.3 meters, $\tau$=500 microseconds, $\rho/t >> 2.4 \times 10^{-4}$. This condition may be satisfied in various ways. For example, a good conductor such as copper may be applied to the bore with a thickness of 1 micrometer. For ease of handling, a preferred method is the use of stainless steel, or some other high resistivity foil of thickness 25 micrometers.

The use of such transmission line coils enables the field to be stabilised within say 50 microseconds, for periods of the order of a few seconds, following the necessary temporary changes in field occasioned by the magnetic resonance procedure. Changes due to the movement of the magnet are thereby essentially eliminated for these periods. Longer term stabilisation is achieved with the aid of an auxiliary pulsed nuclear magnetic resonance signal obtained from a small sample and probe separate from the patient but within the patient's vicinity. Such a "pulsed field frequency lock" is familiar to those skilled in magnetic resonance and will not be considered further. Alternatively, the use of the field-frequency lock may be foregone, and the effects of slow changes in the magnetic field upon the magnetic resonance signal may be corrected with the aid of the computer.

As the amount of space available for the patient and operating table within the magnet is very limited, conventional padding of the type used on an operating table cannot be accommodated. FIGS. 9 and 10 therefore show a modified mattress which is relatively thin having a thickness of the order of 25 mm and yet which provides the necessary protection to the patient against decubitus ulceration.

The mattress for use on top of the plate 44 of the operating table is indicated at 80 and comprises a series of rubber tubes 81 laid side by side and covered with sheets of vinyl 82 and 83 on a top and bottom surface of the whole of the mattress. The tubes extend transversely to the length of the mattress and are parallel and arranged side by side along the full length of the mattress. Alternate ones of the tubes are associated together in two groups. Along each side of the mattress is provided a conduit 84, 85. The conduit 84 contains two parallel supply pipes 85 and 86. The conduit 85 similarly contains two supply pipes (not shown). One of the pipes is associated with one group of the tubes and the other of the pipes is associated with the other of the groups of tubes. The pipes in the conduit 85 act to inflate the tubes while the pipes in the conduit 84 allow deflation of the tubes. In this way alternate ones of the tubes are alternately inflated and deflated over time period of the order of 3–5 minutes. Thus during one such time period the patient is supported on the inflated group of alternate tubes and during the second time period those tubes are deflated and the patient is supported on the other group of alternate tubes. In this way the pressure points on the patient are periodically modified to prevent those pressure points causing reduction in blood supply.

Since various modifications can be made in our invention as herein above described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. Apparatus for use in surgical procedures comprising:

an operating table for receiving a patient for surgery, the table having a first end and a second end;

and a magnetic resonance imaging system for obtaining images of a part of the patient at a series of times through the surgical procedure for analysis by the surgical team to allow the surgical team to monitor the progress of the surgery, the magnetic resonance imaging system comprising:

a magnet for generating high magnetic fields;

a control system for controlling and varying the magnetic fields;

a radio frequency transmission and detection system for eliciting and detecting from the part of the patient nuclear magnetic resonance signals, in response to the magnetic field, including an RF probe arranged to be located adjacent to the part of the patient;

and a computer and display monitor for decoding and displaying the detected signals;

and means mounting the magnet for movement relative to the table in a direction away from the first end of the table from a first position at the table to a second position remote from the table;

the first position of the magnet being arranged such that the part of the patient is positioned in the magnetic field of the magnet while the patient remains in place on the table;

the second position of the magnet being arranged such that the magnet is spaced from the first end of the table by a distance sufficient to allow the surgical team to move around the first end of table and to each side of the table to access the patient and sufficient to allow to allow the surgical team to carry out the surgical procedure.

2. The apparatus according to claim 1 wherein the magnet is shaped to define an inner substantially cylindrical bore with a substantially horizontal axis and wherein the magnet is moved along the horizontal axis.

3. The apparatus according to claim 1 wherein the magnet is shaped to define an inner substantially cylindrical bore with a substantially horizontal axis and wherein the table includes an upstanding mounting base and a substantially horizontal table top mounted thereon, the table top having a cantilever portion extending from the base into the cylindrical bore.

4. The apparatus according to claim 3 wherein there is provided rotational adjustment means for rotating the table top about an axis longitudinal of the table for rolling the patient to one side.

5. The apparatus according to claim 3 wherein there is provided angle adjustment means for tilting the table top about an axis transverse to the table top so as to tilt the patient sufficiently to raise the head of the patient to allow neurosurgery, the table top and the cylindrical bore of the magnet being arranged such that the head of the patient can be located centrally in the bore while the tilted table top projects into one end of the bore.

6. The apparatus according to claim 5 wherein the table top includes a hinged portion at the end thereof for supporting the head of the patient, the hinged portion being pivotal about an axis parallel to said transverse axis and spaced outwardly from the base so as to raise only the head and shoulders of the patient to a height sufficient to allow neurosurgery.

7. The apparatus according to claim 3 wherein the cantilever portion includes a flat plate for receiving the patient and a channel member attached to an underside of the plate and narrower than the plate to support the plate while minimizing the dimensions of the table top to fit in the circular cross-section of the cylindrical bore of the magnet.

8. The apparatus according to claim 7 wherein the table includes a head support for the head of the patient comprising a post projecting through the plate and a swivel support for the post within the channel member.

9. The apparatus according to claim 1 wherein the table includes a mattress thereon comprising a plurality of parallel inflatable tubes transverse to the table and means for inflating and deflating alternate ones of the tubes so as to vary pressure points on the patient from the mattress.

10. The apparatus according to claim 1 wherein the table includes at least parts thereof manufactured from a high electrically resistive and non-ferromagnetic material.

11. The apparatus according to claim 10 wherein at least one of the parts of the table adjacent to the RF probe is coated with a layer of a material which is of an electrical resistance lower than said high electrically resistive material.

12. The apparatus according to claim 1 wherein the RF probe is shaped and arranged such that the RF probe can be actuated in the magnet and such that the RF probe can allow access to the part of the patient for the surgical procedure outside the magnet without the necessity for moving the part of the patient.

13. The apparatus according to claim 12 wherein the RF probe comprises a first probe element for positioning on one side of the part and a second probe element for positioning on an opposed side of the part, the first probe element being removable to allow access to the patient for the surgical procedure.

14. The apparatus according to claim 13 wherein the first and second probe elements are free from wired electrical interconnection so that the first probe element can be removed without disconnecting any wired interconnection.

15. The apparatus according to claim 13 wherein the first and second probe elements each comprise a plurality of parallel planar coils and wherein there is provided means for moving at least one of the coils for tuning and matching the RF probe.

16. The apparatus according to claim 1 wherein there is provided means for stabilizing the field of the magnet after movement of the magnet from said second position to said first position and prior to imaging.

17. The apparatus according to claim 16 wherein the stabilizing means comprises detecting means for detecting changes in the field and means for controlling the field of the magnet.

18. The apparatus according to claim 17 wherein the magnet defines a cylindrical inner bore and wherein the detecting means comprises at least one coil mounted inside the inner bore of the magnet and coaxial therewith and a conductive layer coaxial with the bore and extending along the bore to a distance greater than said at least one coil, the conductive layer being in capacitive electrical connection with said at least one coil and being formed of a material which is non-ferromagnetic, and the conductive layer having an electrical resistance and thickness selected so as to allow currents in said at least one coil which have sufficient bandwidth to detect changes in the field and so as to not interfere with the variation in the field necessary for the imaging techniques.

19. The apparatus according to claim 18 wherein there is provided an RF shielding layer to shield the RF probe from surrounding electrical variations, the shielding layer including the conducting layer.

20. The apparatus according to claim 1 wherein there is provided an RF shielding layer to shield the RF probe from surrounding electrical variations, the shielding layer including an electrically conductive flexible fabric layer adapted to be wrapped around those parts of the patient and table which are outside the magnet.

* * * * *